United States Patent [19]

Drabek

[11] 4,456,559
[45] Jun. 26, 1984

[54] PESTICIDAL N-(3-TRIMETHYLSTANNYLALKYLENE)-N'-PHENYL-SULFONYL OR -BENZOYL-UREAS

[75] Inventor: Jozef Drabek, Oberwil, Switzerland

[73] Assignee: Ciba-Geigy Corporation, Ardsley, N.Y.

[21] Appl. No.: 433,190

[22] Filed: Oct. 6, 1982

[30] Foreign Application Priority Data

Oct. 8, 1981 [CH] Switzerland .................... 6456/81
Oct. 22, 1981 [CH] Switzerland .................... 6750/81
May 28, 1982 [CH] Switzerland .................... 3316/82
Jun. 3, 1982 [CH] Switzerland .................... 3415/82

[51] Int. Cl.$^3$ ............................................. C07F 7/22
[52] U.S. Cl. .................................. 260/429.7; 424/288
[58] Field of Search ................................... 260/429.7

[56] References Cited

U.S. PATENT DOCUMENTS

| | | | |
|---|---|---|---|
| 4,188,334 | 2/1980 | Wehner et al. | 260/429.7 |
| 4,195,029 | 3/1980 | Otto et al. | 260/429.7 |
| 4,202,830 | 5/1980 | Korbanka et al. | 260/429.7 |
| 4,210,595 | 7/1980 | Wirth et al. | 260/429.7 |
| 4,222,950 | 9/1980 | Gitlitz | 260/429.7 |
| 4,301,173 | 11/1981 | Imazaki et al. | 260/429.7 |
| 4,305,883 | 12/1981 | Burley | 260/429.7 |

OTHER PUBLICATIONS

Chemical Abstracts 84 (23) 1649566 (1976).
Chemical Abstracts 84 (9) 59692q (1976).
Chemical Abstracts 70 (1) 4249f (1969).
Chemical Abstracts 75 (5) 36228t (1971).
Chemical Abstracts 64 8231/G (1966).

Primary Examiner—Helen M. S. Sneed
Attorney, Agent, or Firm—Frederick H. Rabin

[57] ABSTRACT

There are described N-(3-trimethylstannylalkylene)-N'-phenylsulfonyl- and -benzoylureas of the formula

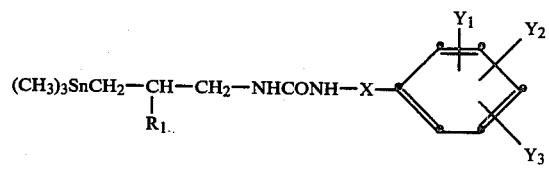

wherein $R_1$ is hydrogen, $C_1$–$C_6$-alkyl or $C_3$–$C_8$-cycloalkyl, X is —CO— or —$SO_2$—, and $Y_1$, $Y_2$ and $Y_3$ independently of one another are each hydrogen, halogen, $C_1$–$C_6$-alkyl, $C_1$–$C_6$-haloalkyl, $C_1$–$C_6$-alkoxy or nitro.

Also described are the production thereof and the use of the novel compounds for combating pests; and the intermediates of the formula

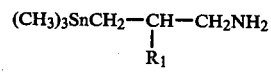

wherein $R_1$ is hydrogen, $C_1$–$C_6$-alkyl or $C_3$–$C_8$-cycloalkyl are likewise described.

7 Claims, No Drawings

PESTICIDAL N-(3-TRIMETHYLSTANNYLALKYLENE)-N'-PHENYL-SULFONYL OR -BENZOYL-UREAS

The present invention relates to N-(3-trimethylstannylalkylene)-N'-phenylsulfonyl- and -benzoylureas, to processes for producing them, and to their use for combating pests.

The N-(3-trimethylstannylalkylene)-N'-phenylsulfonyl- and -benzoylureas have the formula I

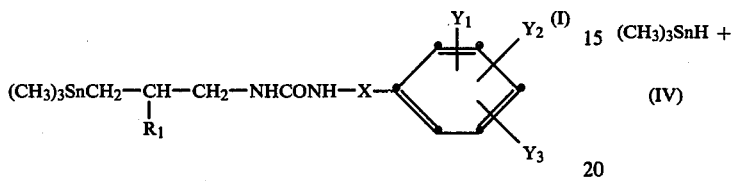

wherein $R_1$ is hydrogen, $C_1$-$C_6$-alkyl or $C_3$-$C_8$-cycloalkyl, X is —CO— or —SO$_2$—, and $Y_1$, $Y_2$ and $Y_3$ independently of one another are each hydrogen, halogen, $C_1$-$C_6$-alkyl, $C_1$-$C_6$-haloalkyl, $C_1$-$C_6$-alkoxy or nitro.

Halogen in this case is fluorine, chlorine, bromine or iodine.

The alkyl, haloalkyl and alkoxy groups denoted by $R_1$, $Y_1$, $Y_2$ and $Y_3$ can be straight-chain or branched-chain. Examples of such groups are, inter alia: methyl, methoxy, trifluoromethyl, ethyl, ethoxy, propyl, isopropyl, n-butyl, n-pentyl and n-hexyl, as well as isomers thereof.

Examples of cycloalkyl groups denoted by $R_1$ are, inter alia: cyclopropyl or cyclohexyl.

Preferred are compounds of the formula I wherein $R_1$ is hydrogen, X is —CO—, $Y_1$, $Y_2$ and $Y_3$ independently of one another are each hydrogen, halogen, $C_1$-$C_6$-alkyl, $C_1$-$C_6$-haloalkyl, $C_1$-$C_6$-alkoxy or nitro; or compounds of the formula I wherein $R_1$ is hydrogen, X is —SO$_2$—, and $Y_1$, $Y_2$ and $Y_3$ independently of one another are each hydrogen, halogen, $C_1$-$C_6$-alkyl, $C_1$-$C_6$-haloalkyl, $C_1$-$C_6$-alkoxy or nitro; or compounds of the formula I wherein $R_1$ is $C_1$-$C_6$-alkyl or $C_3$-$C_8$-cycloalkyl, X is —CO— or —SO$_2$—, and $Y_1$, $Y_2$ and $Y_3$ independently of one another are each hydrogen, halogen, $C_1$-$C_6$-alkyl, $C_1$-$C_6$-haloalkyl, $C_1$-$C_6$-alkoxy or nitro.

Particularly preferred compounds of the formula I are those wherein $R_1$ is hydrogen, X is —CO—, $Y_1$ is halogen, $C_1$-$C_6$-alkyl, $C_1$-$C_6$-haloalkyl, $C_1$-$C_6$-alkoxy or nitro, and $Y_2$ and $Y_3$ independently of one another are each hydrogen, halogen, $C_1$-$C_6$-alkyl, $C_1$-$C_6$-haloalkyl, $C_1$-$C_6$-alkoxy or nitro; or compounds of the formula I wherein $R_1$ is methyl, X is —CO—, $Y_1$ is hydrogen, fluorine, chlorine, methyl, methoxy or nitro, and $Y_2$ and $Y_3$ independently of one another are each hydrogen, fluorine, chlorine, methyl or methoxy.

More especially preferred however are compounds of the formula I wherein $R_1$ is hydrogen, X is —CO—, $Y_1$ is fluorine, chlorine, methyl, methoxy or nitro, and $Y_2$ and $Y_3$ independently of one another are each hydrogen, fluorine, chlorine, methyl or methoxy.

The compounds of the formula I can be produced by the following methods known per se:

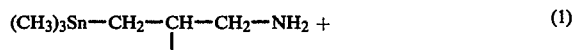

(II)

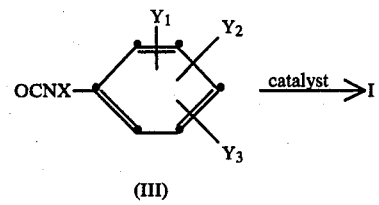

(III)

(IV)

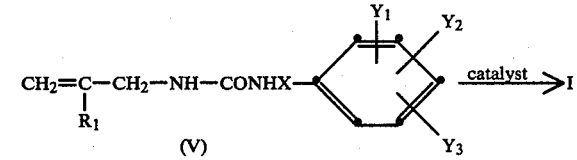

(V)

In the formulae II to V, $R_1$, X, $Y_1$, $Y_2$ and $Y_3$ have the meanings given under the formula I.

The processes are performed under normal pressure and at a temperature of between $-30°$ and $150°$ C., especially between $-10°$ and $100°$ C., and optionally in the presence of a catalyst, for example azoisobutyronitrile, and in a solvent. Suitable solvents are for example: aliphatic, aromatic as well as halogenated hydrocarbons, particularly benzene, xylene, toluene, chloroform or chlorobenzene, also ketones, such as acetone, methyl ethyl ketone, nitriles, such as acetonitrile, and formamides, such as dimethylformamide.

The starting materials of the formulae III to V are known, and can be produced by known methods. The compounds of the formula II are novel, and they likewise form subject matter of the present invention.

The compounds of the formula II can be produced by methods known per se, for example as follows:

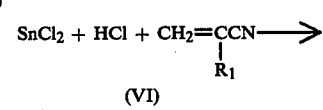

(VI)

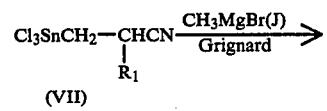

(VII)

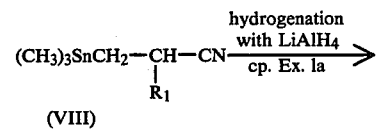

(VIII)

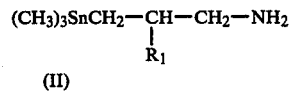

(II)

In the formulae II, VI, VII and VIII, the symbol $R_1$ has the meaning defined under the formula I.

The compounds of the formula I are suitable for combating various pests on animals and plants. They are suitable for combating bacteria and fungi; in particular however for combating insects, for example of the orders: Lepidoptera, Coleoptera, Homoptera, Heteroptera, Diptera, Thysanoptera, Orthoptera, Anoplura, Siphonaptera, Mallophaga, Thysanura, Psocoptera and Hymenoptera, as well as mites and ticks of the order Acarina.

It has been shown that the compounds of the formula I have a strong action both against mites that damage plants, for example mites of the families: Tetranychidae, Tarsonemidae, Eriophidae, Tyroglyphidae and Glycyphagidae, and against ectoparasitic mites and ticks, for example of the families: Ixodidae, Argasidae, Sarcoptidae and Dermanyssidae.

The acaricidal and insecticidal activity can be considerably broadened and adapted to suit given circumstances by the addition of other insecticides and/or acaricides. Suitable additives are for example: organic phosphorous compounds; nitrophenols and derivatives thereof; formamides; ureas; pyrethrin-like compounds, and also carbamates and chlorinated hydrocarbons. The substances of the formula I also have a fungicidal action.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily ued in formulation practice are described, inter alia, in the following publication:

"Mc Cutecheon's Detergents and Emulsifiers Annual", MC Publishing Corp., Ringwood, N.J., 1979.

The pesticidal preparations contain as a rule 0.1 to 99%, particularly 0.1 to 95%, of active substance of the formula I, 1 to 99.9% of a solid or liquid additive, and 0 to 25%, especially 0.1 to 25%, of a tenside. Whereas commercial products are preferably in the form of concentrated compositions, the compositions employed by the end-user are as a rule diluted.

The compositions can also contain additives such as stabilisers, antifoam agents, viscosity regulators, binders and adhesives, as well as fertilisers or other active substances for obtaining special effects.

FORMULATION EXAMPLES FOR LIQUID ACTIVE SUBSTANCES OF THE FORMULA I (%=PERCENT BY WEIGHT)

| 1. Emulsion concentrates | (a) | (b) | (c) |
|---|---|---|---|
| active substance, | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 2. Solutions | (a) | (b) | (c) | (d) |
|---|---|---|---|---|
| active substance | 80% | 10% | 5% | 95% |
| ethylene glycol-monomethyl ether | 20% | — | — | — |
| polyethylene glycol M G 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of the smallest possible drops.

| 3. Granulates | (a) | (b) |
|---|---|---|
| active substance | 5% | 10% |
| kaolin | 94% | — |
| highly dispersed silicic acid | 1% | — |
| attapulgite | — | 90% |

The active substance is dissolved in methylene chloride, the solution is sprayed onto the carrier, and the solvent is subsequently evaporated off in vacuo.

| 4. Dusts | (a) | (b) |
|---|---|---|
| active substance | 2% | 5% |
| highly dispersed silicic acid | 1% | 5% |
| talcum | 97% | — |
| kaolin | — | 90% |

Ready-for-use dusts are obtained by the intimate mixing together of the carriers with the active substance.

FORMULATION EXAMPLES FOR SOLID ACTIVE SUBSTANCES OF THE FORMULA I (%=PERCENT BY WEIGHT)

| 5. Wettable powders | (a) | (b) | (c) |
|---|---|---|---|
| active substance | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active substance is well mixed with the additives and the mixture is thoroughly ground is a suitable mill. Wettable powders which can be diluted with water to give suspensions of the required concentration are obtained.

| 6. Emulsion concentrate | |
|---|---|
| active substance | 10% |
| octylphenol polyethylene glycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| 7. Dusts | (a) | (b) |
|---|---|---|
| active substance | 5% | 8% |
| talcum | 95% | — |
| kaolin | — | 92% |

Dusts ready for use are obtained by mixing the active substance with the carrier and grinding the mixture in a suitable mill.

| 8. Extruder granulate | |
|---|---|
| active substance | 10% |
| sodium lignin sulfonate | 2% |
| carboxymethylcellulose | 1% |
| kaolin | 87% |

The active substance is mixed and ground with the additives, and the mixture is moistened with water. This mixture is extruded and then dried in a stream of air.

| 9. Coated granulate | |
|---|---|
| active substance | 3% |
| polyethylene glycol (M G 200) | 3% |
| kaolin | 94% |

The finely ground active substance is evenly applied, in a mixer, to the kaolin moistened with polyethylene glycol. Dustfree coated granulates are obtained in this manner.

| 10. Suspension concentrate | |
|---|---|
| active substance | 40% |

| 10. Suspension concentrate | |
|---|---|
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active substance is intimately mixed with the additives. There is thus obtained a suspension concentrate from which can be produced, by dilution with water, suspensions of the concentration required.

EXAMPLE 1

(a) Production of 2-methyl-3-trimethylstannyl-propylamine

To a solution of 42.3 g of 2-methyl-3-trimethylstannylpropionitrile (J. Organometall Chem. 86 (1975), 89) in 200 ml of absolute ether is added dropwise at 30° C., in the course of 50 minutes, a suspension of 13.8 g of LiAlH$_4$ in 1000 ml of absolute ether.

The reaction mixture is stirred for two hours, and is then left to stand for twelve hours at 20° C. There are subsequently carefully added dropwise to the reaction mixture at 0° C. 50 ml of water and afterwards 50 ml of 20% sodium hydroxide solution. The precipitate is filtered off, the organic phase is washed with 50 ml of water, and dried over sodium sulfate. The solvent is evaporated off and the product is distilled. There is thus obtained the compound of the formula $$(CH_3)_3SnCH_2CHCH_2NH_2$$
$$|$$
$$CH_3$$

having a boiling point of 73°–75° C./18 Pa.

(b) Production of 1-(2-chlorobenzoyl)-3-(2-methyl-3-trimethylstannylpropyl)-urea 3 g of 2-chlorobenzoylisocyanate are added dropwise at 20° C., with stirring, to a solution of 3.89 g of 2-methyl-3-trimethylstannyl-propylamine in 50 ml of toluene. The reaction mixture is stirred for one hour at 20° C. and for ten hours at 80° C. The reaction mixture is concentrated by evaporation, and the crude product is recrystallised from hexane to thus obtain the compound No. 1 of the formula

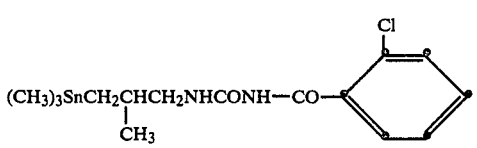

having a melting point of 66°–68° C.

The following compounds are produced in an analogous manner:

(C$_3$)$_3$SnCH$_2$—CH—CH$_2$—NH—CO—NH—CO— 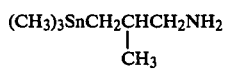
　　　　　　　　|
　　　　　　　R$_1$

| Compound No. | R$_1$ | X | Y$_1$ | Y$_2$ | Y$_3$ | Physical data |
|---|---|---|---|---|---|---|
| 2 | CH$_3$ | —CO— | 3 Cl | 4 Cl | H | m.p.: 18–20° C. |
| 3 | CH$_3$ | —CO— | 2 Cl | H | 6Cl | m.p.: 34–35° C. |
| 4 | CH$_3$ | —CO— | H | H | H | n$_D^{20}$ = 1.5518 |
| 5 | CH$_3$ | —CO— | 2CH$_3$ | H | H | n$_D^{20}$ = 1.5469 |
| 6 | CH$_3$ | —CO— | H | 4Cl | H | m.p.: 80–81° C. |
| 7 | CH$_3$ | —CO— | 2CH$_3$ | 4CH$_3$ | H | n$_D^{20}$ = 1.5431 |
| 8 | CH$_3$ | —CO— | H | 4NO$_2$ | H | m.p.: 69–70° C. |
| 9 | CH$_3$ | —CO— | 2OCH$_3$ | H | H | n$_D^{20}$ = 1.5578 |
| 10 | H | —CO— | 2Cl | H | H | m.p.: 91–92° C. |
| 11 | H | —CO— | 2F | H | H | m.p.: 69–71° C. |
| 12 | H | —CO— | 2F | H | 6F | m.p.: 100–103° C. |
| 13 | H | —CO— | 2Cl | H | 6Cl | m.p.: 124–127° C. |
| 14 | H | —CO— | H | H | H | m.p.: 50–52° C. |
| 15 | H | —CO— | 2CH$_3$ | H | H | m.p.: 45–49° C. |
| 16 | H | —CO— | H | 4Cl | H | m.p.: 97–100° C. |
| 17 | H | —CO— | 3Cl | 4Cl | H | m.p.: 18–19° C. |
| 18 | H | —CO— | 3OCH$_3$ | 4OCH$_3$ | 5OCH$_3$ | m.p.: 109–110° C. |
| 19 | H | —CO— | H | 4NO$_2$ | H | m.p.: 73–74° C. |
| 20 | H | —CO— | 3OCH$_3$ | H | H | n$_D^{20}$ = 1.5555 |
| 21 | H | —CO— | H | CH$_3$<br>$\|$<br>4-C—CH$_3$<br>$\|$<br>CH$_3$ | H | m.p.: 84–85° C. |

(c) Production of N-(3-trimethylstannylpropyl)-N'-phenylsulfonylurea 0.1 ml of triethylamine is added to a solution of 3.7 g of 3-trimethylstannylpropylamine in 50 ml of acetonitrile. There are then added dropwise at 10° C., with stirring, 3 ml of phenylsulfonylisocyanate. The reaction mixture is stirred for one hour at 20° C. and for ten hours at reflux temperature. The reaction mixture is concentrated by evaporation to thus obtain the compound No. 22 of the formula

No. 22 having a refractive index of $n_D^{50°} = 1.5367$.

The following compound is produced in an analogous manner:

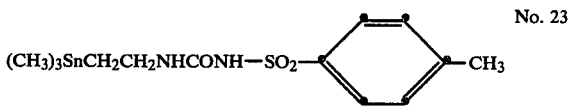

No. 23 m.p.: 163–164° C.

EXAMPLE 2: INSECTICIDAL STOMACH-POISON ACTION

Cotton plants are sprayed with a test solution containing 50, 100 and 200 ppm, respectively, of the compound to be tested. After the drying of the coating, larve of the species Spodoptera littoralis (L$_3$ stage) are settled onto the cotton plants. The test is carried out at 24° C. with 60% relative humidity.

Compounds according to Example 1 exhibit in the above test, against Spodoptera littoralis larvae, the action shown in the following Table.

BIOLOGICAL TEST RESULTS

The Table which follows shows the test results on the basis of the Example given in the foregoing, the evaluation index with regard to the percentage mortality rate being as follows:

A: 70–100% mortality at 50 ppm active-ingredient concentration
B: 70–100% mortality at 100 ppm active-ingredient concentration
C: 70–100% mortality at 200 ppm active-ingredient concentration

| Compound No. | Effectiveness against *Spodoptera littoralis* larvae |
| --- | --- |
| 1 | A |
| 2 | B |
| 3 | A |
| 4 | B |
| 5 | A |
| 6 | C |
| 7 | B |
| 8 | C |
| 9 | B |
| 10 | A |
| 11 | A |
| 12 | A |
| 13 | B |
| 14 | B |
| 15 | C |
| 16 | A |
| 17 | A |
| 18 | C |
| 19 | C |
| 20 | B |
| 21 | B |
| 22 | B |
| 23 | B |

What is claimed is:

1. An N-(3-trimethylstannylalkylene)-N'-phenylsulfonyl- or -benzoylurea of the formula

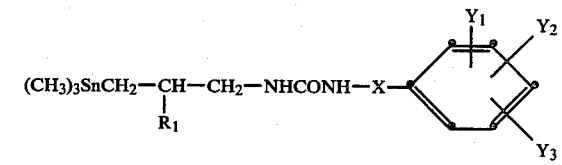

wherein R$_1$ is hydrogen, C$_1$–C$_6$-alkyl or C$_3$–C$_8$-cycloalkyl, X is —CO— or —SO$_2$—, and Y$_1$, Y$_2$ and Y$_3$ independently of one another are each hydrogen, halogen, C$_1$–C$_6$-alkyl, C$_1$–C$_6$-haloalkyl, C$_1$–C$_6$-alkoxy or nitro.

2. A compound according to claim 1, wherein R$_1$ is hydrogen and X is —CO—.

3. A compound according to claim 1, wherein R$_1$ is hydrogen and X is —SO$_2$—.

4. A compound according to claim 1, wherein R$_1$ is C$_1$–C$_6$-alkyl or C$_3$–C$_8$-cycloalkyl.

5. A compound according to claim 2, wherein Y$_1$ is halogen, C$_1$–C$_6$-alkyl, C$_1$–C$_6$-haloalkyl, C$_1$–C$_6$-alkoxy or nitro.

6. A compound according to claim 5, wherein Y$_1$ is fluorine, chlorine, methyl, methoxy or nitro, and Y$_2$ and Y$_3$ independently of one another are each hydrogen, fluorine, chlorine, methyl or methoxy.

7. A compound according to claim 4, wherein R$_1$ is methyl, X is —CO—, Y$_1$ is hydrogen, fluorine, chlorine, methyl, methoxy or nitro, and Y$_2$ and Y$_3$ independently of one another are each hydrogen, fluorine, chlorine, methyl or methoxy.

* * * * *